United States Patent
Weber et al.

(10) Patent No.: US 6,307,112 B1
(45) Date of Patent: Oct. 23, 2001

(54) PROCESS FOR PREPARING PHENOL AND ACETONE BY ACID-CATALYZED CLEAVAGE OF CUMENE HYDROPEROXIDE

(75) Inventors: Manfred Weber, Haltern; Otto Gerlich, Gladbeck; Michael Kleine-Boymann, Bottrop; Werner Pompetzki, Dorsten; Reinhard Sigg, Marl; Christian Michalik, Essen; Jürgen Volke, Gladbeck, all of (DE)

(73) Assignee: Phenolchemie GmbH & Co. KG, Gladbeck (DE)

( * ) Notice: Subject to any disclaimer, the term of this patent is extended or adjusted under 35 U.S.C. 154(b) by 0 days.

(21) Appl. No.: 09/467,238

(22) Filed: Dec. 20, 1999

(30) Foreign Application Priority Data

Dec. 18, 1998 (DE) ............................................... 198 58 770

(51) Int. Cl.[7] .................................................... C07C 37/08
(52) U.S. Cl. ............................................ 568/798; 568/385
(58) Field of Search ..................................... 568/385, 798

(56) References Cited

U.S. PATENT DOCUMENTS 5,254,751 * 10/1993 Zakoshansky ....................... 568/798

* cited by examiner

*Primary Examiner*—S Padmarabhan
(74) *Attorney, Agent, or Firm*—Oblon, Spivak, McClelland, Maier & Neustadt, P.C.

(57) ABSTRACT

Phenol and acetone are prepared by a process comprising homogeneously cleaving cumene hydroperoxide in the presence of acid catalyst in a cleavage apparatus comprising at least one reactor having plug flow characteristics thereby producing a cleavage product; recycling some of the cleavage product stream by combining the recycled cleavage product stream with the cumene hydroperoxide-containing feed stream fed to said cleavage apparatus under the condition that the mass flow ratio of the recycled partial cleavage product stream to the cumene hydroperoxide-containing feed stream sent to the cleavage reactor is less than 10.

16 Claims, 1 Drawing Sheet

PROCESS FOR PREPARING PHENOL AND ACETONE BY ACID-CATALYZED CLEAVAGE OF CUMENE HYDROPEROXIDE

BACKGROUND OF THE INVENTION

1. Field of the Invention

The present invention relates to an improved process for the selective cleavage of cumene hydroperoxide (CHP) into phenol and acetone by the action of an acid.

2. Description of the Background

Phenol is mainly produced internationally from cumene. Cumene is first oxidized to cumene hydroperoxide (CHP). For reasons of selectivity, cumene conversion rates of 20–30% by weight are generally achieved. In a subsequent step, called concentration, the CHP content in the oxidized material is customarily concentrated to 65–90% by weight. What is termed technical-grade CHP is produced. In the subsequent cleavage reaction of the technical-grade CHP product, by action of an acid, usually sulfuric acid, phenol and acetone are produced. After neutralization of the cleavage product, the products are isolated from the cleavage product essentially by distillation in what is termed the work-up stage of a phenol plant.

Both the oxidation reaction and the cleavage reaction are accompanied by unwanted byproduct formation. The cleavage reaction is of particular importance for the selectivity and the yield of the overall process. Parallel to the cleavage of CHP into phenol and acetone, the dimethyl phenyl carbonyl (DMPC) previously formed in the oxidation is dehydrated to α-methylstyrene (AMS). AMS can be hydrogenated in the work-up stage of the process to cumene and thus can be recycled back to the oxidation stage. However, in the CHP cleavage reaction, AMS polymerization reactions or addition reactions between AMS and phenol occur, which reactions lead to the formation of high-boilers (polyAMS and cumylphenols), as a result of which the selectivity and yield of the overall process are substantially adversely affected. The cleavage reaction must, therefore, be conducted industrially in such a manner that the formation of the high-boilers is to the greatest possible extent suppressed.

The industrial cleavage procedure has been described a number of times. Generally, the cleavage reaction is conducted in an ideally mixed apparatus. The heat released in the highly exothermic CHP cleavage reaction is dissipated either by evaporating acetone (evaporative cooling, cf U.S. Pat. No. 5,463,136) or by external coolers such as described, for example, in U.S. Pat. No. 4,358,618. U.S. Pat. No. 4,358,618 describes how the selectivity of such a cleavage can be improved by downstream tubular reactors. The procedure is as follows. In an ideally mixed main reactor, technical-grade CHP is cleaved to residual CHP concentrations of 0.5–5% by weight by adding an acid at temperatures in the range from 50–90° C. Under these conditions, at least 40% by weight of the DMPC present reacts with CHP to form dicumyl peroxide (DCP) and water. In the downstream first tubular reactor, the CHP is cleaved to residual contents below 0.4% by weight, and the temperatures in this reaction are similar to those in the main reactor. In the second tubular reactor, finally, the DCP formed previously is cleaved into AMS, phenol and acetone. Temperatures in the range of 120–150° C. are established. Therefore, the main reactor and the first tubular reactor can be summarized as "CHP cleavage" and the second tubular reactor can be called "DCP cleavage". The idea of thermally post-treating the cleavage product after the actual CHP cleavage reaction, as described in U.S. Pat. No. 4,358,618. in a further tubular reactor has long been known and has been described in U.S. Pat. No. 2,757,209. Temperatures above 100° C., preferably from 110–120° C., are specified for the DCP cleavage. The purpose of this thermal post-treatment is then the complete dehydration of DMPC to form AMS. In addition to the high-boilers already formed in the CHP cleavage, further high-boilers are formed in the DCP cleavage.

Published patent application SU 11 31 865 A also describes a two-stage process, wherein, in the first stage, the cleavage of CHP is performed, while, in the second stage, DCP formed in the first stage is cleaved. SU 11 31 865 A teaches, furthermore, that for heat dissipation, based on each stage, recycling product from one stage to the feed of the other stage in a ratio of 20:1 and not feeding the sulfuric acid used as catalyst until the second stage, so that further recycling of cleavage product from the DCP cleavage reaction (second stage) to the feed of the CHP cleavage reaction (first stage) in a volumetric ratio of 1:1–:10 is necessary in order to transfer the acid to the first stage.

Studies conducted by the inventors have shown that the rate of cleavage of cumene hydroperoxide dCHP/dt is proportional to the CHP concentration. Thus, for a given conversion rate, the space-time yield in an ideally mixed reactor as described in U.S. Pat. No. 4,358,618 is always lower than in a tubular reactor.

The volume of such an ideally mixed apparatus is, therefore, always greater than that of a tubular reactor if the same CHP flow rates in each case are to be cleaved to give the same CHP final contents in each case. The amounts of cleavage product having residual CHP contents which are found in an ideally mixed apparatus are correspondingly greater, compared with a tubular reactor. However, for safety reasons, it is advantageous to keep the volume in cleavage reactors as low as possible and simultaneously provide a high heat transfer surface between reacting technical-grade CHP and cooling medium. This is achieved if the cleavage is conducted in reactors having plug flow characteristics, that is, for example, tube-bundle heat exchangers. In this case, the product can flow both on the tube side and in the shell space if, here, plug flow characteristics are established by special internals (deflection baffles). Small reaction volumes and large heat exchange surfaces, i.e. reactors having large specific surface areas per unit volume for heat transfer, ensure that even in the event of failure of, for example pumps, despite the highly exothermic cleavage reaction of CHP, no safety-critical states occur.

The use of a plurality of series-connected tube-bundle heat exchangers for the cleavage of technical-grade CHP has already been described in DBP 1 112 527. In this case, CHP is dispersed in excess sulfuric acid and the dispersion can then be passed through the coolers in which the heat of reaction is dissipated; sulfuric acid and organic phase are then separated from each other. The sulfuric acid is recycled and the cleavage product is neutralized and worked-up. By means of this so-called heterogeneous cleavage reaction, however, high selectivities cannot be achieved, since, in the circulating sulfuric acid, side reactions with the formation of high-boilers proceed to an increased extent.

Therefore, similarly to U.S. Pat. Nos. 4,358,618, 5,254, 751 also describes a homogeneous CHP cleavage, that is to say the sulfuric acid used only in small amounts dissolves in the reaction mass. In contrast to U.S. Pat. No. 4,358,618, according to U.S. Pat. No. 5,254,751, however, the CHP cleavage reaction is conducted in three series-connected coolers at from 45–75 ° C., these obviously being tube-bundle heat exchangers, in which the reaction mass flows through the shell space under plug flow conditions. The reaction product, in this case, is partially recirculated to achieve high selectivities, so that some of the CHP cleavage product arising downstream of the last cooler is recycled and admixed with the CHP stream flowing into the first cooler, the mass flow ratio of recycled circulated stream to the inflowing CHP stream, what is termed the circulation ratio λ, is said to be in the range from 10–25. Furthermore, an embodiment of the process is that in the effluent from the reactor system, from 0.3–1.5% by weight residual contents of CHP must be present. The cleavage product is then treated by being heating to a temperature of 80–110° C. under plug flow conditions in order to convert the DCP formed in CHP cleavage into phenol, acetone and AMS.

FIG. 1 is an outline diagram of this CHP and DCP cleavage reaction described in U.S. Pat. No. 5,254,751. In reactor 1, the CHP cleavage occurs under plug flow conditions. Some of the cleavage product is branched off via line 3 and, after addition of acid as catalyst via line 6, mixed with the feed stream or technical-grade CHP via line 4, before this mixture enters reactor 1. The remainder of the cleavage product is fed via line 5 to the tubular reactor 2 for DCP cleavage. The circulation ratio λ is given by the ratio of circulation rate in line 3 upstream of the CHP admixture to the CHP feed stream via line 4. The cleavage product circuit is generated via a pump 7 (circulation pump). The cleavage product which, for example, flows freely from the circuit, is pumped by means of a further pump 8 to the downstream DCP reactor 2.

Although the use of reactors having plug flow characteristics gives, in principle, as described above, the advantage of higher space-time yields and thus smaller reaction volumes, because of the high circulation rates required, the volume of these apparatuses increases again, and, furthermore, large piping and pumps are required to implement these high circulation rates. A need, therefore, continues to exist for a more efficient process of cleaving CHP which provides also for a reduction of capital equipment costs.

SUMMARY OF THE INVENTION

Accordingly, one object of the present invention is to provide an improved process for the acid-catalyzed homogeneous cleavage of CHP into phenol and acetone which, in addition to a high selectivity, provides a reduction in capital costs.

Briefly, this object and other objects of the present invention as hereinafter will become more readily apparent can be attained in a process for preparing phenol and acetone by homogeneously cleaving cumene hydroperoxide in the presence of acid catalyst in a cleavage apparatus comprising at least one reactor having plug flow characteristics thereby producing a cleavage product, recycling some of the cleavage product stream by combining the recycled cleavage product stream with the cumene hydroperoxide-containing feed stream fed to said cleavage apparatus under the condition that the mass flow ratio of the recycled partial cleavage product stream to the cumene hydroperoxide-containing feed stream sent to the cleavage reactor is less than 10.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

The FIGURE is a diagram of a reactor embodiment of the invention showing at least one reactor having plug flow characteristics.

DETAILED DESCRIPTION OF THE PREFERRED EMBODIMENTS

Figure 1:
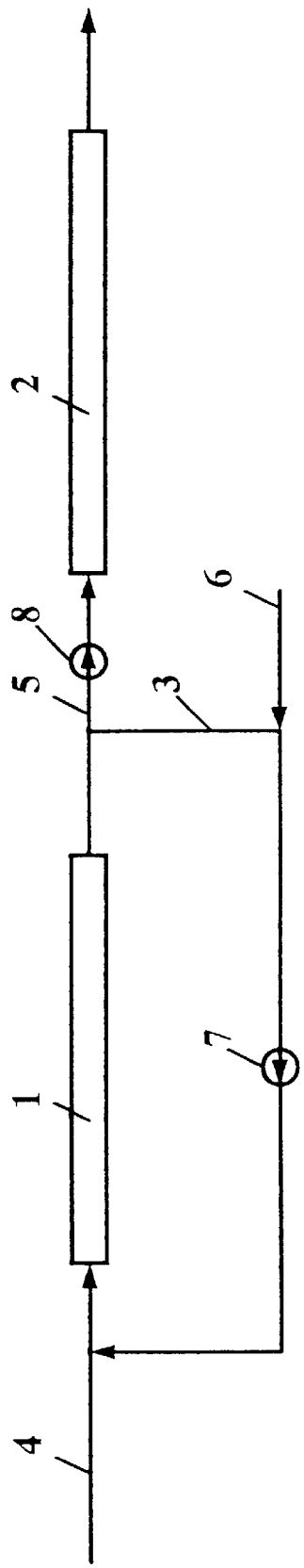

Surprisingly, it has been found, contrary to the teaching of U.S. Pat. No. 5,254,751, that a circulation ratio λ of from 10–25 is not required in order to achieve high selectivities in the CHP cleavage reaction. Rather, it has been found that by lowering the circulation ratio below 10, preferably from 2–9, particularly preferably from 5–7, under otherwise identical conditions, even improved selectivities can be achieved.

The investigations of the present invention have revealed that under otherwise identical reaction conditions in a given CHP cleavage apparatus, when the circulation ratio is increased, the addition of acid as catalyst must also be increased in order to achieve, unchanged, CHP cleavage to the same given residual concentration in the cleavage product, with the same residence time of the reaction products in the reactor system. The more strongly acidic environment during the cleavage reaction, however, clearly favors the formation of byproducts and thus impairs selectivity. Therefore, in the invention, circulation ratios as small as possible must always be sought.

As mentioned above, for safety reasons, it must be ensured that the heat of reaction released during the highly exothermic CHP cleavage reaction can be dissipated at any time and at any point to avoid uncontrollable reactor states, that is even when in case of breakdown, the flow through the cleavage apparatus comes to a halt. In order to avoid redundant designs of technical components having corresponding monitoring units, in practice it is preferred to provide sufficiently large heat-exchange surfaces which even in the event of breakdowns reliably ensure sufficiently high heat dissipation. Since, as the circulation ratio decreases, the feed concentration of CHP into the CHP cleavage apparatus increases (since, due to low circulation rates, the technical-grade CHP is less highly dilute), for safety reasons, correspondingly larger heat-exchange surfaces are thus also required, in particular at the sites of high CHP concentration, therefore, especially at the entry to the cleavage apparatus. Decreasing the circulation ratio, therefore, usually has a bottom limit for a given cleavage apparatus for safety considerations. With conventional CHP cleavage apparatuses such as the tube-bundle heat exchangers preferably used, this leads to the fact that according to the invention, particularly preferably, circulation ratios of from 5–7 are set, since these may still be readily made safely. Appropriate dimensioning of the apparatuses can ensure, for example, that even in the case of loss of flow through the reactors, the heat of reaction can be dissipated to the environment by free convection in the reaction mass or other measures.

For this purpose the first reactor, for example, can be erected vertically as a tube-bundle apparatus, the reaction mass flowing from bottom to top in the tubes through the apparatus and the technical-grade CHP being added at the bottom. In this case, if the circulation stream is lost, the heat being liberated can still be adequately dissipated by the development of free convection. Another possibility is to construct the pump for the circulation stream with redundancy, here, for example, two rotary pumps are arranged in parallel and should run simultaneously. In the event of loss of one pump, the circulation can still be maintained adequately by the second pump. Furthermore, in the event of loss of the circulation stream the system can still be adequately flushed with cumene and thus the reaction mass can be cooled and diluted. All of these are measures which can be conducted by current technology, and they obviously can also be employed in combination in order to manage small circulation ratios safely.

Even relatively small circulation ratios below 5 can thus be implemented in reactors which have a specific surface area per unit volume for heat exchange (that is a ratio of heat-exchange surface area to enclosed reaction volume) $\geq 500$ m$^2$/m$^3$. In this case also, the reactor is preferably dimensioned so that in the event of loss of flow there is an overall coefficient of heat transfer sufficiently high for the enclosed reaction volume in order to ensure safe heat dissipation.

In addition to this advantage of higher selectivity, and thus a decrease of the residue, however, technical advantages are also gained by the procedure of the invention using small circulation ratios. In the case, for example, of a circulation ratio of 7, for a plant which generates 200,000 metric t/yr of phenol, a circulation rate of 530 m$^3$/h is needed, while for a circulation ratio of 17, a circulation rate of 1200 m$^3$/h must be set. If, further, from reaction times which are conventional industrially, approximately one minute is assumed for the CHP cleavage, in the case of a circulation ratio of 7, a reaction volume of approximately 9 m$^3$ is necessary, while in the case of a circulation ratio of 17, in contrast, a reaction volume of approximately 20 m$^3$ is required. Thus the size and hence the capital costs for cleavage reaction plants having smaller circulation ratios are considerably lower than those for cleavage plants having high circulation ratios.

Another advantage of the process of the invention is that, by lowering the circulation ratios, lower residual CHP concentrations in the cleavage product can also be established without, as a result, inevitably making byproduct formation and thus the selectivity worse. Although, in order to decrease the residual CHP concentration the addition of acid must be increased, a result of which is that byproduct formation is promoted, this effect can be at least compensated for or even overcome, owing to the increase in selectivity, by decreasing the circulation ratio, so that at least without losses in selectivity, lower residual CHP concentrations can be achieved. In a procedure having a residual CHP concentration of, for example, 1% by weight or more, the risk of "breakthrough" of CHP into downstream vessels is greater than in the case of procedures having low residual concentrations. Correspondingly, the safety expenditure in the case of plants having high residual CHP concentration in the cleavage product must be higher.

Therefore, low residual concentrations are always to be desired.

Using the process of the invention, preferably, a technical-grade CHP is cleaved which comprises from 65–90% by weight of CHP. The remainder essentially consists of cumene; in addition, byproducts formed in the oxidation of cumene are present to a small extent.

The reactors are selected as a function of the CHP content of the technical grade CHP to be cleaved, taking into consideration the safety aspects in such a manner that as small a circulation ratio as possible can be achieved. Customarily, a CHP cleavage apparatus of the invention comprises one or more series-connected reactors having plug flow characteristics, preferably tube-bundle heat exchangers, the reaction mixture either flowing through the tube space, which is preferred, or through the shell space. Suitable reactors of the invention include plate- and spiral-heat exchangers which likewise have plug flow characteristics. In particular, but not exclusively, for small circulation ratios, preferably, reactors having plug flow characteristics and a specific surface area for heat exchange per unit volume of 500 m$^2$/m$^3$ are used.

Downstream of the last CHP cleavage reactor, some of the cleavage product stream is removed by separation. This separated cleavage product partial stream is recycled and combined with the feed stream of technical-grade CHP to be cleaved upstream of or in, based on the flow, the first cleavage reactor. Preferably, the admixture is performed upstream of entry into the first reactor. The acid required as catalyst is preferably added to the recycled cleavage product partial stream before this stream is combined with the feed stream of fresh technical-grade CHP. Preferably, the catalyst is sulfuric acid. Preferably, sufficient acid is added and is dissolved in the reaction mixture so that the residual CHP concentration in the cleavage product ranges from 0.1–1.5% by weight, preferably from 0. 1–0.3% by weight. Customarily, for this purpose, an acid concentration of from 50–500 ppm by weight is required in the reaction mixture. The cleavage reaction of the invention is performed preferably in a cleavage apparatus having from three to six sequentially-arranged cooled tube-bundle heat exchangers. The technical grade CHP diluted with the recycled cleavage product flows through either the tube space or through the shell space. In the event of flow through the shell space, by installing deflection baffles or longitudinal baffles, the piston flow characteristic can be improved. In the case of flow in the tube space, multipath apparatuses can also be used.

The homogeneous cleavage reaction is preferably conducted at from 45–75° C. and reaction pressures of from 1–5 bar absolute. In addition, it can be advantageous to add water to a small extent to the reaction mixture in addition to the added acid, preferably from 0.3–1% by weight of water. Preferably, the water is likewise added to the recycled cleavage product partial stream, if appropriate together with the acid. The tube-bundle heat exchangers which dissipate the heat of reaction are preferably cooled with water. The residence times of the reaction mixture in the CHP cleavage apparatus are generally from 0.5–10 minutes.

With an appropriate design of conventional apparatuses, the apparatus can be used in the present invention, without risks to safety. Circulation ratios of recycled cleavage product partial stream to feed stream of technical-grade CHP of preferably from 5–7 may be employed. In addition to savings in apparatus costs and operating costs, improvements in the cumene yield of approximately 0.5 percentage points or more can thus be achieved, which, against the background of an annual global phenol production of approximately 7 million metric tons, is a significant improvement in economic efficiency.

The unrecycled portion of the CHP cleavage product is, as, for example, in U.S. Pat. No. 5,254,751, preferably fed to a suitable cleavage apparatus for the DCP cleavage, preferably to at least one tubular reactor in which a DCP cleavage is performed in a known manner prior to the further work-up of the stream for production of phenol and acetone.

Having now generally described the invention, a further understanding can be obtained by reference to certain specific Examples which are provided herein for purpose of illustration only and are not intended to be limiting unless otherwise specified.

EXAMPLES

Example 1 (Comparative Example)

In a cleavage apparatus having the basic structure of FIG. 1, technical-grade CHP having a CHP content of 67% by weight is reacted to a product having a residual content of 1.0% by weight CHP in the cleavage product. A circulation ratio λ of 17 is established here. The addition of sulfuric acid as catalyst is matched accordingly.

Three series-connected tube-bundle heat exchangers (reactor 1 in FIG. 1) serve as CHP cleavage reactors. The reaction temperature is 50° C., and the reaction pressure is 1 bar absolute.

The CHP cleavage product produced comprises 0.21% by weight of high-boilers, which are essentially polymerized AMS and cumylphenols. The CHP cleavage is followed by cleavage of DCP.

Example 2 (Invention)

The CHP cleavage of Example 1 is operated under otherwise identical conditions with a circulation ratio of 7. Acid addition employed and a residual CHP concentration of 0.25% by weight in the CHP cleavage product is set. The cleavage product likewise comprises 0.21% by weight of high-boilers.

Despite the lower residual CHP concentration, which can be achieved in Example 1 only by higher acid addition which promotes byproduct formation, in this case, by lowering the circulation ratio, the same selectivity as in Comparative Example 1 is achieved. Cleavage reactors and piping can be dimensioned to be correspondingly smaller. In addition, the lower residual CHP content offers safety advantages for the downstream plant components.

Example 3 (Invention)

The CHP cleavage of Example 1 is operated under otherwise identical conditions, including the residual CHP concentration of 1.0% by weight in the cleavage product, at a circulation ratio of 7. The high-boiler content in the cleavage product is 0.16% by weight. By decreasing the circulation ratio, the selectivity was markedly increased in comparison with Example 1. In comparison to Example 2, it is shown that, by increasing the residual CHP concentration at a low circulation ratio, selectivity can be improved.

Examples 4–8 (Invention)

The CHP cleavage reaction of Example 1 is operated under otherwise identical conditions at various circulation ratios in such a manner that, with a matched acid addition, a residual CHP concentration of 0.25% by weight is always established in the cleavage product. In addition, the high-boiler content in the cleavage product is determined in each case as a function of the circulation ratio.

The results are shown in Table 1.

TABLE 1

High-boiler concentration at differing circulation ratios at constant residual CHP concentration

| Example | 4 | 5 | 6 | 7 | 8 |
| --- | --- | --- | --- | --- | --- |
| Circulation ratio | 9 | 8 | 7 | 6 | 5 |
| High-boiler concentration (%) | 0.25 | 0.23 | 0.21 | 0.19 | 0.17 |

It is clear here that, at constant residual CHP concentration, but lower circulation ratio, the high-boiler formation decreases, and the selectivity, therefore, increases.

Example 9

In a cleavage apparatus having a basic structure as that shown in U.S. Pat. No. 4,358,618, technical-grade CHP having a CHP content of 67% by weight is first cleaved in an ideally mixed apparatus at 50° C. to a residual CHP content of 2.75% by weight and is then cleaved in a tubular reactor at 50° C. to a residual CHP concentration of 0.2% by weight. The cleavage product comprises 0.20% by weight of high boilers.

As Examples 4–8 demonstrate, higher selectivities are achievable by the process of the invention.

The disclosure of German priority Application Number 19858770.8 filed Dec. 18, 1998 is hereby incorporated by reference into the present application.

Obviously, numerous modifications and variations of the present invention are possible in light of the above teachings. It is, therefore, to be understood that within the scope of the appended claims, the invention may be practiced otherwise than as specifically described herein.

What is claimed as new and is intended to be secured by Letters Patent is:

1. A process for preparing phenol and acetone, comprising:

homogeneously cleaving cumene hydroperoxide in the presence of acid catalyst in a cleavage apparatus comprising at least one reactor having plug flow characteristics thereby producing a cleavage product;

recycling some of the cleavage product stream by combining the recycled cleavage product stream with the cumene hydroperoxide-containing feed stream fed to said cleavage apparatus under the condition that the mass flow ratio of the recycled partial cleavage product stream to the cumene hydroperoxide-containing feed stream sent to the cleavage reactor is less than 10.

2. The process as claimed in claim 1, wherein the reactors have a specific surface area for heat transfer per unit volume of $\geq 500$ m$^2$/m$^3$.

3. The process as claimed in claim 1, wherein the cleavage apparatus comprises one or more series connected tube-bundle heat exchangers as reactors for cleavage of cumene hydroperoxide.

4. The process as claimed in claim 3, wherein the cleavage apparatus has from three to six tube-bundle heat exchangers as reactors for the cleavage of cumene hydroperoxide.

5. The process as claimed in claim 3, wherein the reaction mixture flows through the tubular space of the tube-bundle heat exchangers.

6. The process as claimed in claim 4, wherein the reaction mixture flows through the tubular space of the tube-bundle heat exchangers.

7. The process as claimed in claim 1, wherein the mass flow ratio of recycled, partial cleavage product stream to the cumene hydroperoxide-containing feed stream is in the range of 2–9.

8. The process as claimed in claim 7, wherein said mass flow ratio is in the range of 5–7.

9. The process as claimed in claim 1, wherein the residual concentration of cumene hydroperoxide in the cumene hydroperoxide cleavage product ranges from 0.1–1.5% by weight.

10. The process as claimed in claim 9, wherein the residual concentration of cumene hydroperoxide in the cumene hydroperoxide cleavage product ranges from 0.1–0.3% by weight.

11. The process as claimed in claim 1, wherein cumene hydroperoxide is cleaved at a temperature ranging from 45–75° C. and a pressure of 1–5 bar absolute.

12. The process as claimed in claim 1, wherein the residence time of the reaction mixture in the cumene hydroperoxide cleavage apparatus ranges from 0.5–10 minutes.

13. The process as claimed in claim 1, wherein the cumene hydroperoxide content of the feed stream ranges from 65–90% by weight.

14. The process as claimed in claim 1, wherein the acid catalyst is sulfuric acid.

15. The process as claimed in claim 1, wherein the acid concentration in the cumene hydroperoxide-containing material in the reactors ranges from 50–500 ppm.

16. The process as claimed in claim 1, wherein the cumene hydroperoxide-containing material in the reactors contains water in a concentration ranging from 0.3–1% by weight.

* * * * *

UNITED STATES PATENT AND TRADEMARK OFFICE
CERTIFICATE OF CORRECTION

PATENT NO.    : 6,307,112 B1
DATED         : October 23, 2001
INVENTOR(S)   : Manfred Weber et al.

It is certified that error appears in the above-identified patent and that said Letters Patent is hereby corrected as shown below:

<u>Title page,</u>
*Primary Examiner*, "S Padmarabhan" should read -- S. Padmanabhan --.

<u>Column 2,</u>
Line 1, "4,358,618. in" should read -- 4,358,618, in --;
Line 19, "1:1:10" should read -- 1:1-1:10 --;
Line 45, "for example" should read -- for example, --;
Line 61, "U.S. Pat. Nos. 4,358,618, 5,254,751" should read -- U.S. Patent 4,358,618, U.S. Patent 5,254,751 --;
Line 67, "45-75 º C.," should read -- 45-75º C., --.

<u>Column 3,</u>
Line 13, "heating" should read -- heated --;
Line 18, "reactor 1" should read -- reactor 1 --;
Line 22, "reactor 1." should read -- reactor 1. --.

<u>Column 4,</u>
Line 42, "dilute)" should read -- diluted) --;
Line 54, "that even" should read -- that, even --.

<u>Column 5,</u>
Line 61, "technical grade" should read -- technical-grade --.

<u>Column 6,</u>
Line 20, "0.1-0.3%" should read -- 0.1-0.3% --;
Line 26, "technical grade" should read -- technical-grade --.

UNITED STATES PATENT AND TRADEMARK OFFICE
CERTIFICATE OF CORRECTION

PATENT NO. : 6,307,112 B1
DATED : October 23, 2001
INVENTOR(S) : Manfred Weber et al.

It is certified that error appears in the above-identified patent and that said Letters Patent is hereby corrected as shown below:

<u>Column 8,</u>
Line 9, "high boilers" should read -- high-boilers --;
Line 12, "German priority Application Number" should read -- German Priority Application --;
Line 40, "of ≧" should read -- of ≥ --;
Line 42, "series connected" should read -- series-connected --.

Signed and Sealed this

Tenth Day of September, 2002

*Attest:*

*Attesting Officer*

JAMES E. ROGAN
*Director of the United States Patent and Trademark Office*